US008153374B2

(12) United States Patent
Dinges

(10) Patent No.: US 8,153,374 B2
(45) Date of Patent: Apr. 10, 2012

(54) HEAT FLOW POLYMERASE CHAIN REACTION METHODS

(75) Inventor: Warren L. Dinges, Seattle, WA (US)

(73) Assignee: HeatFlow Technologies, Inc., Seattle, WA (US)

( * ) Notice: Subject to any disclaimer, the term of this patent is extended or adjusted under 35 U.S.C. 154(b) by 308 days.

(21) Appl. No.: 12/396,949

(22) Filed: Mar. 3, 2009

(65) Prior Publication Data

US 2009/0220984 A1 Sep. 3, 2009

Related U.S. Application Data

(60) Provisional application No. 61/033,153, filed on Mar. 3, 2008.

(51) Int. Cl.
*C12Q 1/68* (2006.01)
*C12P 19/34* (2006.01)

(52) U.S. Cl. ........................ 435/6.12; 435/6.1; 435/6.11

(58) Field of Classification Search ........................ None
See application file for complete search history.

(56) References Cited

U.S. PATENT DOCUMENTS

| | | | |
|---|---|---|---|
| 4,683,202 | A | 7/1987 | Mullis |
| 6,171,785 | B1 | 1/2001 | Higuchi |
| 2004/0018506 | A1 | 1/2004 | Koehler et al. |
| 2005/0190813 | A1 | 9/2005 | Schick |
| 2005/0227265 | A1 | 10/2005 | Barany et al. |
| 2006/0029965 | A1 | 2/2006 | Wittwer et al. |
| 2006/0192960 | A1 | 8/2006 | Rencs et al. |

OTHER PUBLICATIONS

Pfaffl et al., "Relative expression software tool (REST ©) for group-wise comparison and statistical analysis of relative expression results in real-time PCR," Nucleic Acids Research 2002, vol. 30, No. 9, e36, pp. 1-10.*

Liu et al., "DNA Amplification and Hybridization Assays in Integrated Plastic Monolithic Devices," Analytical Chemistry, 2002, vol. 74, pp. 3063-3070.*

T. Hatakeyama and F.X. Quinn; Fundamentals and Applications to Polymer Science; Thermal Analysis; 1994; p. 1-17, 65-68: John Wiley & Sons Ltd; West Sussex, England.

T. Hatakeyama, Z. Liu; Handbook of Thermal Analysis; 1998; p. 1-41, 66-128, 156-162; John Wiley & Sons Ltd; West Sussex, England.

M. Brown, P. Gallagher; Handbook of Thermal Analysis and Calorimetry; 2008; p. 1-54; vol. 5; Elsevier; Amsterdam.

H. Hinz and F. Schwarz; Measurement and Analysis of Results Obtained on Biological Substances with Differential Scanning Calorimetry; Pure Appl. Chem. (IUPAC); 2001; p. 745-759; vol. 73.

Diamond Differential Scanning Calorimeter; High Sensitivity Thermal Analysis; brochure; 2003; 12 pgs; PerkinElmer, Inc.; Shelton, CT.

Differential Scanning Calorimeter—Jade DSC; brochure; 2006; 8 pgs; PerkinElmer, Inc.; Shelton, CT.

G. Bruylants, J. Wouters, and C. Michaux; Differential Scanning Calorimetry in Life Science: Thermodynamics, Stability, Molecular Recognition and Application in Drug Design; Current Medicinal Chemistry; 2005; pp. 2011-2020; Bentham Science Publishers, Ltd.

Nomenclature for Thermal Analysis—IV; Pure & Appl. Chem.; 1981; pp. 1597-1603; vol. 53; Pergamon Press, Ltd; Great Britain.

Introduction to Quantitative PCR, Methods and Application Guide; Brochure; 2006; 50 pgs; Stratagene.

International Search Report and Written Opinion for PCT/US09/35881 dated May 12, 2009.

Differential Scanning Calorimetry; Apr. 24, 2009; 9 pages; http://pslc.ws/macrog/dsc.html.

Schwarz, Federick P., Enthalpy of Solution of Carbohydrates Using a Modified Differential Scanning Calorimeter, 1996, Journal of Solution Chemistry, vol. 25, No. 5, pg. 471, Abstract Only.

Applied Biosystems: Real-Time Vs. Traditional PCR, [online tutorial, internal reference: Part #: 4371001 Rev A; Stock #: 117GU11-01]. [retrieved as early as May 6, 2009] Retrieved from the Internet <URL: http://www6.appliedbiosystems.com/support/tutorials/pdf/rtpcr_vs_tradpcr.pdf), 15 pages.

Bhadeshia, H.K.D.H.: Differential Scanning Calorimetry, Research Paper, University of Cambridge, Materials Science & Metallurgy (2002); [online], [retrieved as early as May 6, 2009] Retrieved from the Internet <URL: http://www.msm.cam.ac.uk/phase-trans/2002/Thermal2.pdf), 9 pages.

Polymerase chain reaction. [online]. Wikipedia, 2007 [retrieved on Dec. 7, 2007]. Retrieved from the Internet: URL:http://en.wikipedia.org/wiki/PCR, 12 pages.

Differential scanning calorimetry. [online]. Wikipedia, 2007 [retrieved on Jun. 22, 2007]. Retrieved from the Internet: URL:http://en.wikipedia.org/wiki/Differential_scanning_calorimetry, 3 pages.

Differential thermal analysis. [online]. Wikipedia, 2007 [retrieved on Dec. 7, 2007]. Retrieved from the Internet: URL:http://en.wikipedia.org/wiki/Differential_Thermal_Analysis, 2 pages.

Differential scanning calorimetry. [online]. Wikipedia, 2007 [retrieved on Dec. 7, 2007]. Retrieved from the Internet: URL:http://en.wikipedia.org/w/index.php?title=Differential_scanning_calorimetry&printable=yes, 4 pages.

* cited by examiner

*Primary Examiner* — Young J Kim

(57) ABSTRACT

Methods and systems for polymerase chain reactions (PCR) that are capable of detecting amplified DNA during or after the PCR process. The methods and systems may utilize DSC or DTA analysis techniques.

42 Claims, 15 Drawing Sheets

HEAT FLOW POLYMERASE CHAIN REACTION METHODS

CROSS-REFERENCE TO RELATED APPLICATION

This application claims the benefit of U.S. Provisional Application No. 61/033,153, filed Mar. 3, 2008.

BACKGROUND

The field of the disclosure relates to polymerase chain reactions (PCR) and, particularly, to methods and systems for detecting PCR products during or after the PCR process.

Generally, polymerase chain reaction (PCR) is a process for amplifying nucleic acids and involves the use of two oligonucleotide primers, an agent for polymerization, a target nucleic acid template and successive cycles of denaturation of nucleic acid and annealing and extension of the primers to produce a large number of copies of a particular nucleic acid segment. With this method, segments of single copy genomic DNA can be amplified more than 10 million fold with very high specificity and fidelity. PCR methods are disclosed in U.S. Pat. No. 4,683,202, which is incorporated herein by reference for all relevant and consistent purposes.

PCR was first developed in the 1980s as a method of copying template DNA. The reaction may include DNA polymerase (e.g., Taq-polymerase), building block deoxynucleotide triphosphates (dATP, dTTP, dGTP and dCTP), sequence-specific forward and reverse primer oligonucleotides, a reaction buffer, the template DNA and a thermal cycler. The fundamental PCR reaction begins with a first step (denaturing/melting) at a higher temperature which melts apart the template-paired strands of DNA. This is followed by a second step at a lower temperature (primer annealing) in which the forward and reverse primers attach to the conjugate sequences on the template DNA. The third step (extension/elongation) is at an intermediate temperature in which the DNA polymerase extends the primers by adding paired deoxynucleotides and thus creating the copied deoxynucleic acid strands (cDNA). These three steps are repeated sequentially with a doubling of the product oligonucleotide during each cycle. Typically, the reaction is run for 15 to 40 total cycles.

In practice, the PCR process begins with one long melting step to ensure complete denaturing/melting of the template DNA. Older PCR methods (such as end-point PCR) separate the amplification cycles from the analysis of the amplified products. In other words, a thermal cycler is used to perform the PCR and then the products are analyzed in a separate, second process. This analysis usually involves gel electrophoresis that separates products based on size/molecular weight, or direct oligonucleotide sequencing that determines the actual A, T, C and G base sequences of the product oligonucleotides. The sequence analysis of oligonucleotide products is now more typically performed on complex, automated capillary sequencing systems.

In the late 1990s, a new method of PCR was developed called real-time PCR. This method combined the thermal cycling and detection of the growing oligonucleotide products. These real-time PCR methods employ fluorescent dyes. The commercial real-time PCR systems all integrate a thermal-cycler and an optical fluorescent detection system. These systems typically use a personal computer, but some are stand-alone microprocessor based systems. They also have various numbers of sample wells, including 12-, 24-, 32-, 48-, 96- and 384-well formats.

Product formation and the temperature of product oligonucleotide melting are conventionally determined by thermal analysis of product oligonucleotides via fluorescent based real-time PCR devices. These methods utilize the temperature dependent fluorescence of the sample and require an optical pathway and fluorescent dyes. A need exists for devices and methods for determining oligonucleotide product formation that do not require optical pathways or fluorescent-based analysis.

SUMMARY

Generally, according to embodiments of the present disclosure, a successful polymerase chain reaction may be detected by measuring and comparing the thermal properties of a thermal reference sample and a PCR reaction solution after amplification. These methods (referred to herein as "Heat Flow PCR" or "HF-PCR™") may utilize differential scanning calorimetry (DSC) or differential thermal analysis (DTA) to detect the presence of oligonucleotide products. The methods rely upon the detection of the thermal changes within the PCR sample relative to the reference sample.

Embodiments of the disclosure simplify PCR methods and PCR reaction systems and, particularly, reaction instrumentation. The simplified methods and systems may make PCR more cost-effective. For example, Heat Flow PCR may allow for the direct detection of the amplified oligonucleotides without reliance on an optical pathway. The Heat Flow PCR method generally does not rely on product detection using gel electrophoresis, oligonucleotide sequencing, or fluorescent techniques (binding dyes, FRET, etc.). The instrumentation for the Heat Flow PCR also generally does not require an optical pathway as conventionally used in fluorescent real-time PCR instruments.

In one aspect of the present disclosure, a method of detecting the formation of amplified DNA in a PCR reaction solution during or after PCR amplification comprises applying heat to the PCR reaction solution. Heat is also applied to a thermal reference solution. The temperature of the PCR reaction solution and the temperature of the thermal reference solution are measured.

In another aspect, a method of detecting the formation of amplified DNA in a PCR reaction solution during or after PCR amplification comprises removing heat from the PCR reaction solution. Heat is also removed from a thermal reference solution. The temperature of the PCR reaction solution and the temperature of the thermal reference solution are measured.

In a further aspect, a method of detecting the formation of amplified DNA in a PCR reaction solution during or after PCR amplification comprises generating heat from a first heater and applying the heat to the PCR reaction solution. Heat is generated from a second heater and the heat is applied to a thermal reference solution. The power input to the first heater is measured and the power input to the second heater is measured.

In yet another aspect, a method of detecting the formation of amplified DNA in a PCR reaction solution during or after PCR amplification comprises removing heat from the PCR reaction solution by use of a first cooling system. Heat is removed from a thermal reference solution by use of a second cooling system. The power input to the first cooling system is measured and the power input to the second cooling system is measured.

In one aspect, a method of detecting the formation of amplified DNA in a PCR reaction solution during or after PCR amplification comprises applying heat to the PCR reaction solution and to a thermal reference solution. The differential temperature between the PCR reaction solution and the thermal reference solution is measured.

In another aspect, a method of detecting the formation of amplified DNA in a PCR reaction solution during or after PCR amplification comprises removing heat from the PCR reaction solution and removing heat from a thermal reference solution. The differential temperature between the PCR reaction solution and the thermal reference solution is measured.

One aspect of the present disclosure includes a system for detecting amplified DNA in a PCR reaction solution during or after PCR amplification. The system includes a sample block having a plurality of sample wells for receiving reaction components. At least one heater in the block is disposed to heat each sample well. Sample temperature sensors are disposed for sensing a temperature in each well. The system also includes a computer programmed to monitor at least one of (1) the output of sample temperature sensors and (2) the power input to a plurality of heaters. The computer is further programmed to compare at least one of (1) the output of at least two of the temperature sensors and (2) the power input to at least two heaters to detect the formation of amplified DNA.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the drawings.

DETAILED DESCRIPTION

Figure 1:
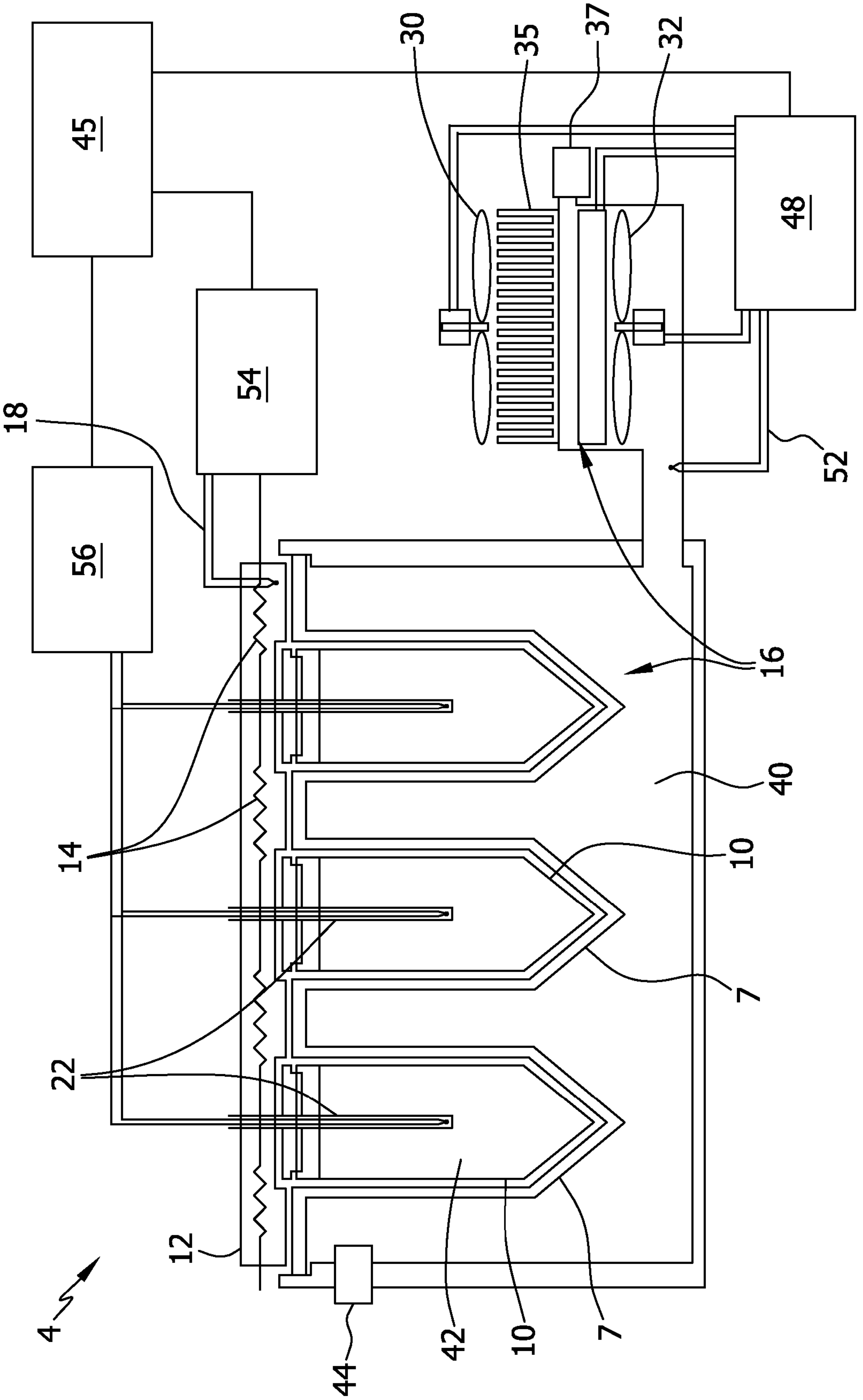
FIG. 1 is a partially schematic cross-section view of a sample block of one embodiment of the present disclosure with thermal control features being illustrated.

The present disclosure is directed to polymerase chain reaction methods and systems for detecting amplified DNA. The methods and systems are capable of utilizing both DTA and DSC analysis techniques.

Polymerase Chain Reaction Methods

Basic polymerase chain reactions (PCR) generally include a number of reagents. A PCR reaction solution may include, for example, DNA polymerase (e.g., Taq-polymerase), "building block" deoxynucleotide triphosphates (e.g., dATP, dTTP, dGTP and dCTP), at least two sequence specific primer oligonucleotides (forward and reverse or sense and antisense), a reaction buffer (e.g., an aqueous saline solution with some other salts such as $MgCl_2$) and a template DNA to be amplified. Other components may be added to optimize the PCR reaction and to limit DNA secondary structures such as, for example, dimethylsulfoxide (DMSO), glycerol and Dimethylformamide (DMF). Taq-polymerases bound with antibodies, optimized structure and differing specificity/error rates may be used to create different results and hot-start capabilities. As generally appreciated within the field of the disclosure, the selection of primers, template DNA and magnesium or manganese concentrations may be varied to optimize the PCR reaction.

DSC and DTA techniques may perform better with liquid reagents and samples that have been degassed to remove dissolved gases therein. The dissolved gases in liquid samples may "boil" out of the sample during a thermal analysis, which creates an apparent transition and change in baseline. Thus, DSC and DTA systems may perform best with degassed reagents and liquids. The use of non-degassed reagents, however, would likely only affect the first few cycles of the HF-PCR™ process.

Conventional PCR methods involve a series of steps including denaturation, annealing and elongation. Generally, the specific temperatures and length of time at each step is frequently adjusted for specific conditions. Generally, the denaturation step is performed at a temperature from about 90° C. to about 100° C.; the annealing step is performed at a temperature of from about 50° C. to about 65° C.; and the elongation step is performed at a temperature from about 65° C. to about 80° C.

PCR methods are generally capable of doubling the DNA template at least about 25 times and, in other embodiments, from about 25 to about 40 times.

Generally, the PCR methods herein utilize differential thermal analysis (DTA) or a comparatively more complex differential scanning calorimetry (DSC) process.

DTA devices analyze a sample and reference contained within a single oven. The oven is heated and cooled and the differential temperature of the sample relative to the reference is measured during the changing temperatures of the sample and reference. This differential temperature profile is the fundamental data output. DTA methods are generally described and illustrated in "Handbook of Thermal Analysis and Calorimetry-Recent Advances, Techniques, and Applications," Vol. 5, Eds. Michael E. Brown and Patrick K. Gallagher, Elsevier Science, Amsterdam, 2008; "Handbook of Thermal Analysis," Eds. T. Hatekeyama and Zhenhai Liu, John Wiley and Sons, New York, 1998; and "Thermal Analysis Fundamentals and Applications to Polymer Science," T. Hatakeyama and F. X. Quinn, John Wiley and Sons, New York, 1994, each of which is incorporated herein by reference for all relevant and consistent purposes.

According to the DSC process, a sample and reference are heated and cooled inside a thermal-block or oven. The heat flow into and out of the sample relative to the reference is measured and provides the temperature and specific heat of the phase transitions and reactions of interest. DSC instruments quantify the differential heat flow (and temperature) into the sample relative to the reference while DTA devices only provide the temperature of thermal transitions.

DSC instruments and methods of the present disclosure may be either heat flux or power compensated devices. In heat flux DSC, the sample and reference are in direct thermal contact and in a single oven. This oven is heated and the relative heat flow and temperature between the sample and reference are quantified. In power compensated DSC, individual heaters compensate for the heat flow into the sample relative to the reference. The power required to compensate for the heat flow into the sample relative to the reference is the fundamental data output of power compensated DSC. Most DSC instruments also use a personal computer for instrument control and analysis, but some are stand-alone microprocessor based devices.

In one embodiment, the PCR methods of the present disclosure involve real-time PCR, rather than end-point PCR. In end-point PCR, a PCR reaction is run in a thermal cycler for a predefined number of cycles (usually 25-40). The product amplified oligonucleotide is then only analyzed after the reaction cycling is complete, when the PCR reaction is usually well into the plateau stage.

For real-time PCR, the reaction is monitored during the ongoing PCR reaction thermal cycles to provide real-time information regarding the PCR reaction products at each step of the thermal cycling. This monitoring may occur during any of the PCR stages (denaturing, annealing, elongation), but in practice most real-time PCR instruments only monitor the PCR reaction at one of the stages during each thermal cycle. The specific stage to monitor the reaction can depend on the nature of the detection system used. The heat of melting of the product oligonucleotide will present or appear as an endothermic peak on warming from elongation to denaturing temperatures and as an exothermic peak on cooling from denaturing to annealing temperatures. The cycle number of the first detection of the oligonucleotide melt transition beyond threshold ($C_t$) can be used to both qualitatively and quantitatively detect the amplified DNA product. Thermal changes within the sample may be measured by DTA or DSC to generate a thermal melt curve to analyze the presence of amplified DNA.

It is contemplated within the scope of the present disclosure to use an end-point PCR system. However, an end-point HF-PCR™ system is likely to be more susceptible to problems from primer-dimers and other non-specific amplification products. The HF-PCR™ system may be better utilized in a real-time PCR system where the first identification of the thermal changes in the sample can give better specificity to the results. The cycle at which a thermal change is first detectable in a real-time DSC or DTA device may also be used to better assess the validity of the amplification product results.

DSC and DTA techniques may be improved with addition of co-solvents or solutes that alter the relative stability of single and/or double stranded DNA. These additives (e.g., sucrose) may increase the heats of melting of DNA which increases the sensitivity of both DTA and DSC HF-PCR™ systems.

According to one embodiment of the present disclosure, amplified DNA is detected by applying heat to the PCR reaction solution and to a thermal reference solution. The thermal reference solution is utilized to mimic the thermal properties of the PCR reaction solution and, particularly, the thermal properties of the solution prior to amplification of template DNA in the solution.

The presence of amplified DNA may be detected by a DTA analysis method or a DSC analysis method. In embodiments that include DTA analysis, the temperature of the PCR reaction solution and thermal reference solution may be measured. The presence of amplified nucleotide products is indicated by a difference in the temperature of the PCR reaction solution and reference solution. In embodiments that include power-compensated DSC analysis, the power input into the first heater and the power input into the second heater are measured. The presence of nucleotide products is indicated by a difference in the power input to the heaters. In embodiments that include heat flux DSC analysis, the differential temperature between the PCR reaction solution and the thermal reference solution is measured. The presence of nucleotide products is indicated once the differential temperature has been related to an enthalpy change in the PCR reaction solution.

In another embodiment, amplified DNA products are detected by removing heat rather than applying heat to the PCR reaction solution and thermal reference solution. Heat may be removed from the PCR reaction solution and the thermal reference solution by use of, for example, a cooling system. In embodiments that include DTA analysis, the presence of nucleotide products is indicated by a difference in the temperature of the PCR reaction solution and reference solution. In embodiments that include power-compensated DSC analysis, the presence of nucleotide products is indicated by a difference in the power input to the cooling systems. In embodiments that include heat flux DSC analysis, the presence of nucleotide products is indicated once the differential temperature has been related to an enthalpy change in the PCR reaction solution.

Generally, the temperatures of the PCR reaction solution and the thermal reference solution (DTA), the power inputs to the heaters or coolers that supply or remove heat from the PCR reaction solution and thermal reference sample (power-compensated DSC), or the differential temperature between the reaction solution and reference solution (heat flux DSC) are measured while heat is applied or removed. However, in some embodiments the measurements are made after the heat has been applied or removed. For instance, in an end-point PCR analysis method, the amplified DNA is typically analyzed after the reaction cycling is complete.

The thermal reference solution is utilized to match the thermal properties of the PCR reaction solution before amplification of DNA. The reference sample generally does not produce amplified DNA during the thermal cycles applied to the samples within the reaction block. Accordingly, after several thermal cycles, the thermal properties of the PCR reaction solution(s) have changed while the thermal properties of the reference solution are generally the same.

In some embodiments, the thermal reference analysis is conducted at a different time from the sample analysis. For example, data related to the thermal reference sample may be stored. Subsequently measured data related to the sample may be compared to the stored thermal reference data. This is possible in either DTA systems and power-compensated DSC systems. For heat flux DSC systems, the sample and thermal reference pair are typically analyzed at about the same time.

In some embodiments, the thermal reference solution may be a "no-template control sample", i.e., the reference solution has the same composition as the initial PCR reaction solution but does not contain template DNA. In another embodiment, the reference solution contains an amount of reaction buffer, the reaction buffer being generally the same type used in the PCR reaction solution. In other embodiments, the thermal reference solution also contains deoxynucleotide triphosphates with the composition of the deoxynucleotide triphosphates being generally the same as used in the PCR reaction solution. Further, the reference solution may also contain an amount of the same primer oligonucleotides used in the PCR reaction solution. Further, the thermal solution may contain amounts of primers and additives used in the PCR reaction solution.

In some embodiments, the mass of the thermal reference solution is generally equal to the mass of the PCR reaction solution. However, more or less of the reference solution may be used without departing from the scope of the present disclosure. Generally, when more or less of the reference solution is used, this fact is accounted for in the microprocessor, computer or in the software such that the computer or microprocessor may accurately detect the presence of amplified DNA.

In some embodiments, a second template DNA is amplified. The formation of second amplified DNA may be detected similar to the first amplified DNA by both DTA and DSC analysis techniques by comparing the thermal properties of the second PCR reaction solution to the thermal reference solution. The first template DNA and second template DNA may be generated from the same source of DNA or may be derived from different DNA sources. The first DNA and second DNA may be amplified sequentially or simultaneously and detection of the presence of amplified products may be performed sequentially or simultaneously.

In some embodiments, an amplification process may be performed wherein DNA is amplified in two PCR reaction solutions with differing compositions. The compositions of the two PCR reaction solutions may vary in terms of template DNA and the types of buffer solution, co-solvents and other additives utilized in the PCR solutions. The compositions of the two PCR reaction solutions may also vary in terms of the relative amounts of components. If two different PCR reaction solutions are utilized, two different thermal reference solutions may also be utilized to mimic the thermal properties of the respective PCR reaction solutions.

The heat may be applied or removed in cycles including cycles that correspond to the amplification procedure. Detection of amplified products may be performed after the cycles are complete or measured during the cycles.

Generally the amplified DNA detection methods do not require the use of optics, gel electrophoresis, oligonucleotide sequencing or fluorescence.

PCR System

A PCR system according to one embodiment of the present disclosure detects PCR products during or after PCR amplification. The system includes a sample block (synonymously "reaction block") and a computer. The block includes a plurality of sample wells for receiving reaction components (e.g., PCR reaction solutions or a thermal reference solution). For purposes of the present disclosure, the term "solution" as used in "PCR reaction solution" or "thermal reference solution" is conterminous with "sample."

A heating and cooling system controls the flow of heat into and out of each sample well and sample temperature sensors are disposed for sensing a temperature in each well. The computer is programmed to monitor the sample temperature sensors for monitoring heat flow into and out of each sample well. The presence of nucleotide products is indicated by a difference in the temperature of the PCR reaction solution and a reference solution (DTA) or by a difference in the power applied to the PCR reaction solution and the reference solution (DSC) as measured by the computer.

The system may use a variety of heating devices (and cooling devices in some instances). For instance, direct-contact conduction, convection and radiant heating (and cooling) and latent heat transfer devices may be utilized. Devices may include electric heaters, refrigerated cooling and thermoelectric heaters and coolers.

The system may utilize any type of temperature sensor including, without limitation, thermocouples, thermistors, resistance thermometers, infrared thermometers and silicon band gap temperature sensors.

The system may generally utilize DTA or DSC analysis techniques as further described herein.

DTA System

Figure 2:
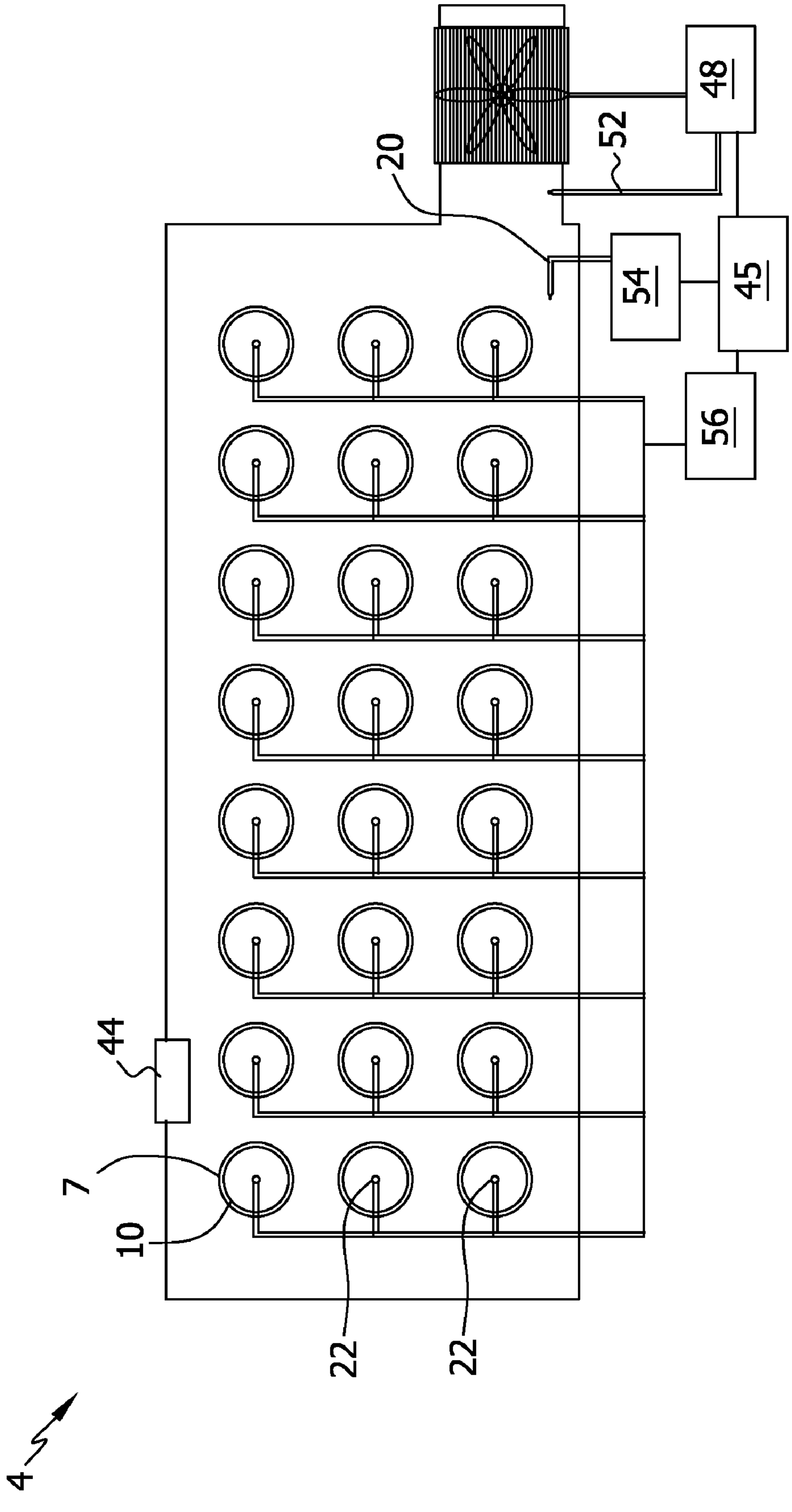
FIG. 2 is a partially schematic top view of the sample block of FIG. 1 with thermal control features being illustrated.

Referring now to FIGS. 1 and 2, a reaction block of a differential thermal analysis (DTA) system is generally indicated by reference numeral 4. The sample block 4 includes a number of sample wells 7 formed therein. While an array of 24 wells is illustrated (FIG. 2), any configuration and number of wells may be included in the reaction block 4 without departing from the scope of the present disclosure. Because of the relatively few sample wells (24), the DTA system illustrated is suitable for, for example, use as a design and testing platform. Systems well-suited for use as a production device typically have at least about 50 wells, at least about 100 wells or even at least about 1000 wells.

Each well 7 may be sized and shaped to receive a sample tube 10 therein. Each sample tube 10 may be sized and shaped to hold the PCR reagents described above.

High thermal conductivity materials are appropriate for the block 4 and sample tubes 10. The reaction block 4 may be suitably composed of an inert material capable of repeatedly withstanding temperatures of up to about 125° C. In one embodiment, the block is composed of a metal such as, for example, stainless steel.

The sample tubes 10 may be constructed of any material that is a good thermal conductor and that is chemically inert relative to the PCR reaction reagents. Suitable materials include metals and thermoplastics such as polypropylene. In some embodiments and especially in systems utilizing DSC analysis, no sample tube is required. Alternatively, liners such as TEFLON liners may be utilized or aluminum or silver pans may be used as the sample tubes.

In one embodiment, the sample tubes are a film that is applied to the reaction block to cover the sample wells 7. Typically, the lids 12 are also inert toward the PCR reaction reagents. The lids 12 may be removably attached to the tubes 10 and may be friction-fit with the tubes.

A block heating and cooling system 16 extends through the block 4 and is in thermal communication with the sample tube 10 and the reagents therein. The illustrated block heating and cooling system 16 is a Peltier heating and cooling unit that transfers heat by convection; however, other suitable heating and cooling devices are contemplated for use in accordance with the present disclosure. For example, other suitable heaters include resistive heaters with conduction or convection transfer and Peltier heaters with conduction transfer. Other suitable coolers include, for example, ambient air cooled with convection transfer, liquid nitrogen-latent heat with convection transfer, refrigerated coolers with conduction or convection transfer and Peltier coolers with convection or conduction transfer. As used herein, the terms "heater", "furnace" and "oven" are interchangeable.

The illustrated block heating and cooling system 16 includes an external fan 30, internal fan 32 and heat exchanger 35. The block heating and cooling system 16 operates by forcing air through an inlet valve 37 and though the heat exchanger 35. The air is heated or cooled in the heat exchanger 35 as appropriate during the thermal cycle of the amplification method. The block heating and cooling system 16 is controlled by a controller unit 48. The heated/cooled air is circulated into a heating/cooling chamber 40 where the sample wells 7 are located. Through conduction, heat transfers to or from the samples 42 within the sample tubes 10. The air exits the system through an outlet valve 44. The block heating and cooling system 16 may include inlet or outlet filters (not shown) to filter incoming and outgoing air. The filters may be located near (upstream or downstream) the inlet valve 37 and outlet valve 44.

Sample temperature sensors 22 (e.g., a thermocouple or thermistor) are disposed within the samples 42. The temperature sensors 22 are shown as embedded in the system; however, the sensors may be disposed in thermal contact with the wells 7 or sample tubes. 10.

The sample 42 temperature is controlled by a sample temperature controller 56. The temperature controller 56 may control the temperature of each sample in a multiplexed manor, i.e., in a sequential fashion wherein the controller sequentially processes the temperatures of the samples 42. A block temperature sensor 20 (FIG. 2) (e.g., a thermocouple or thermistor) is disposed distally from the sample and well. An air temperature sensor 52 monitors the temperature of the air used to heat and cool the samples 42.

The system further includes a lid 12 for covering the block 4 and the wells 7 therein. The lid 12 includes recesses therein, and each recess is sized to receive a top portion of one of the sample tubes 10. The lid 12 includes a lid heater 14 for heating the lid, and a lid temperature sensor 18 (e.g., a thermocouple or thermistor). The temperature of the lid 12 may be controlled by a lid temperature controller 54.

Figure 3:
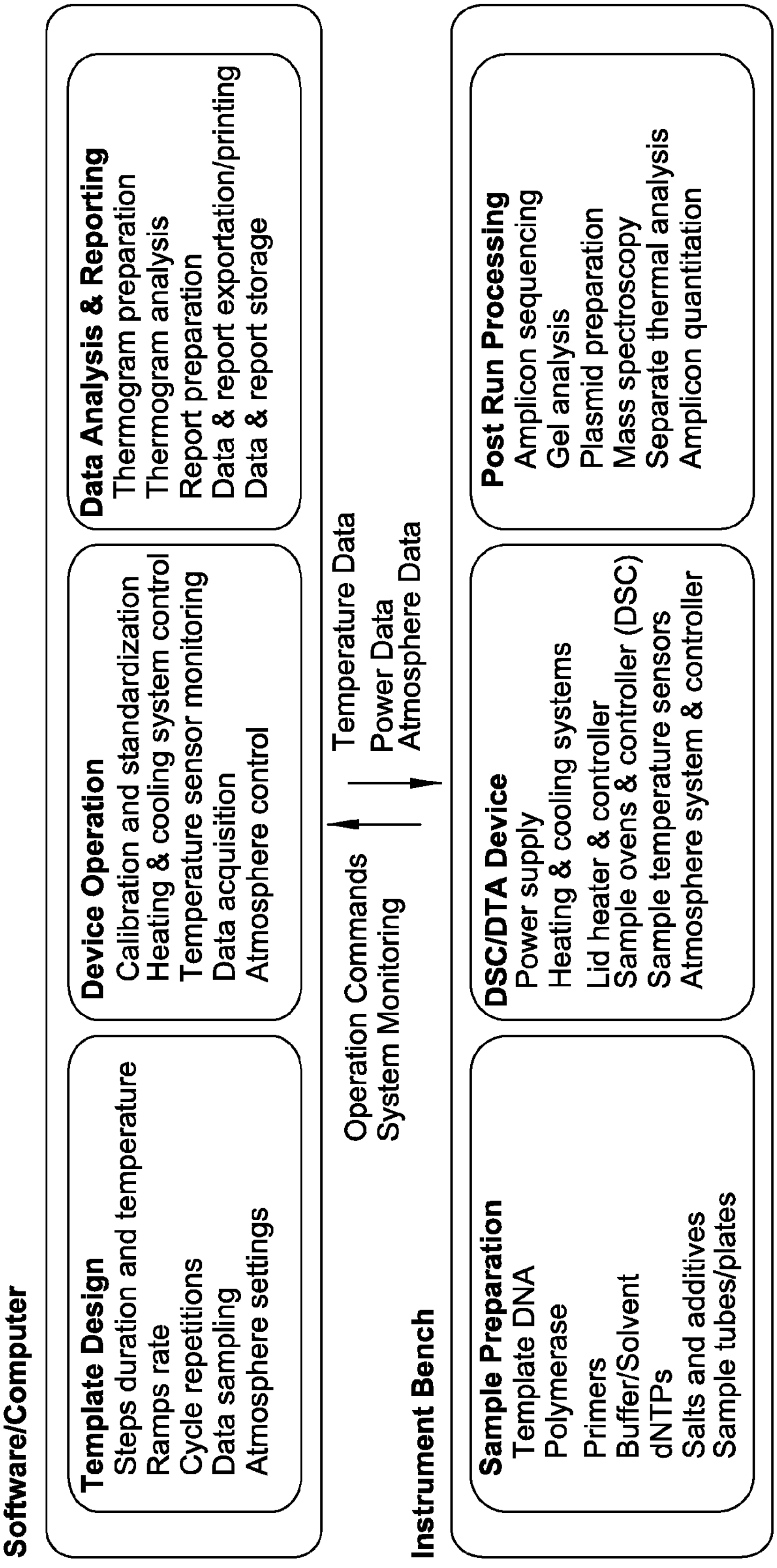
FIG. 3 is a block diagram illustrating functions and interactions between a sample block and a computer of a DTA or DSC system.

The DTA system includes a computer 45. The computer 45 may be used to operate the system and analyze data. Among the specific functions of the computer is to control the "thermal cycler" or heating and cooling systems 14, 16, count the number of cycles, monitor the sample temperatures and analyze the product differential thermograms. The functions and interactions between the block 4 and computer 45 are illustrated in FIG. 3.

Figure 4:
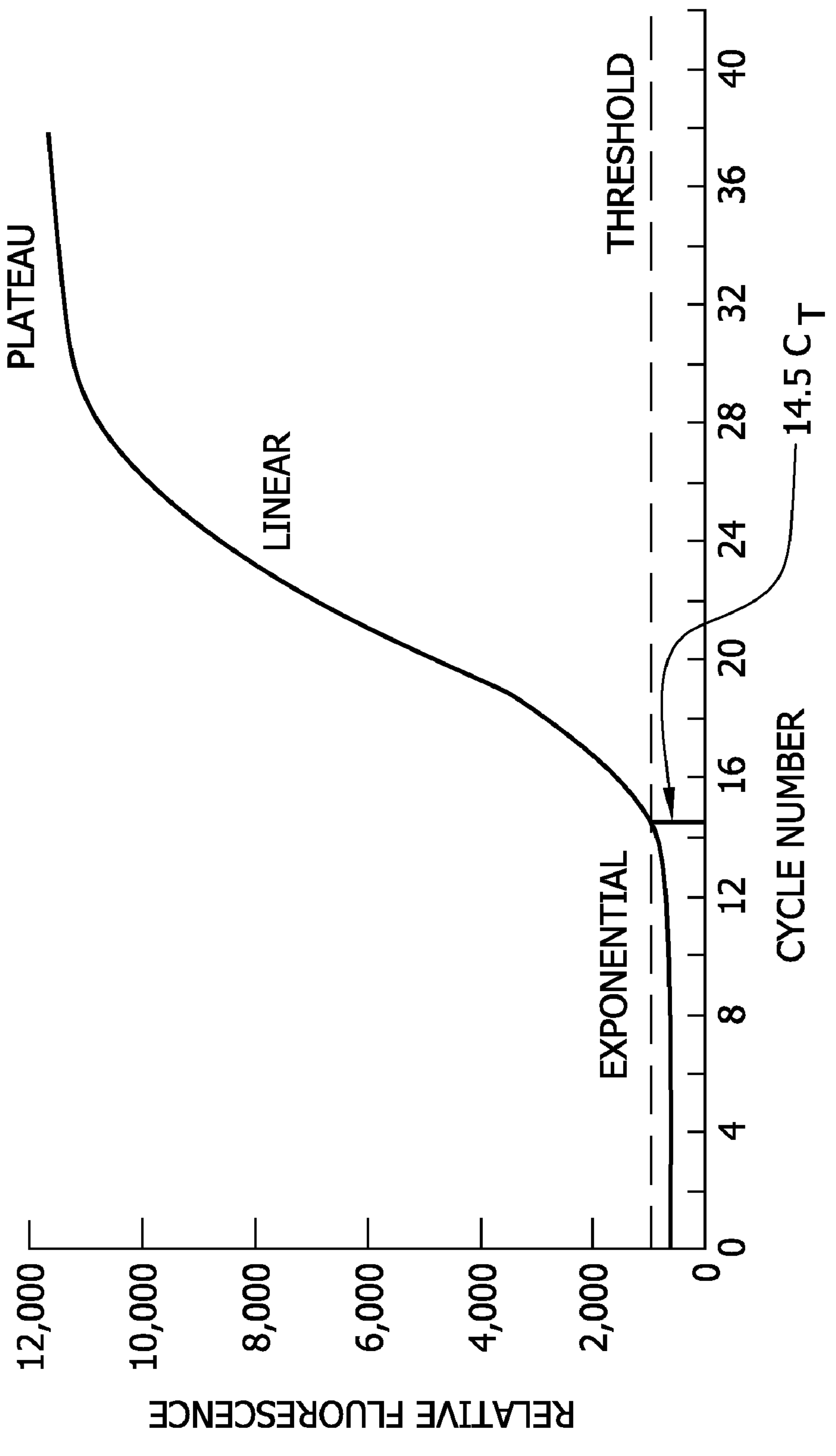
FIG. 4 is a chart illustrating the cycle threshold, $C_t$, at which the sample fluorescence is first detectably different from the background fluorescence as measured in a real-time fluorescent PCR instrument.
Figure 5:
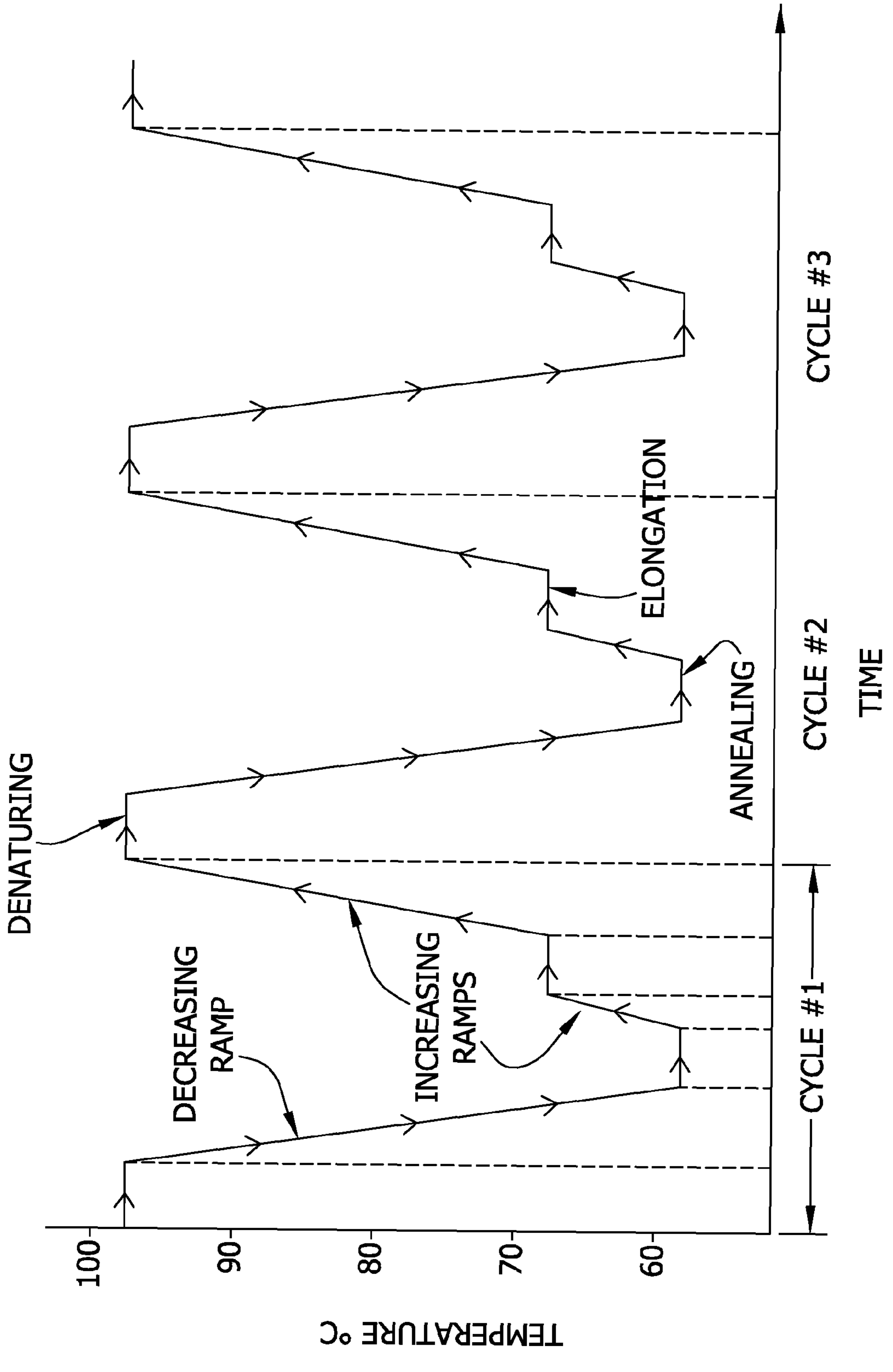
FIG. 5 is a chart illustrating the transfer of heat into samples of a DTA or DSC system during denaturing, annealing and elongation reaction stages.

The thermal cycle for transfer of heat into the samples for each of the PCR reaction stages (i.e., denaturing, annealing, elongation) is illustrated in FIG. 5. Generally, the DTA system monitors the sample and reference temperatures as the system cycles through the PCR stages. The output data from the DTA system is the differential temperatures of the samples relative to the reference, based on the absolute temperature. Each of the sample temperature profiles match that of the reference until there is sufficient quantity of newly generated oligonucleotide amplification products that the melting energy requirements alter the thermal profiles. The PCR cycle number at which the temperature profile of a sample is first detectably different from the reference temperature profile is referred to as the cycle threshold ($C_t$). The $C_t$ is equivalent to the cycle threshold in real-time fluorescent PCR instruments, i.e., the point at which the sample fluorescence is first detectably different from background fluorescence as illustrated in FIG. 4.

Figure 6A:
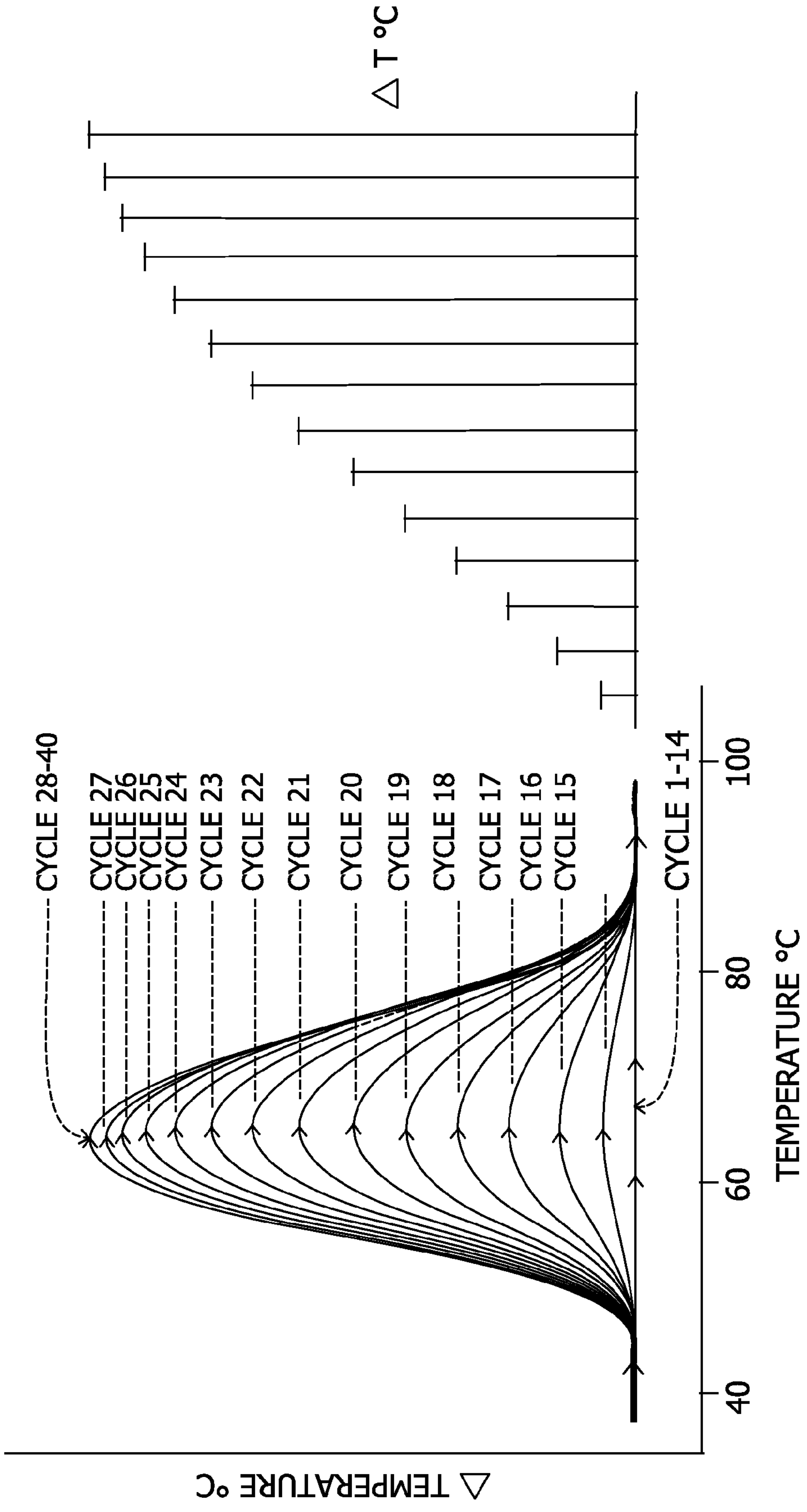
FIGS. 6A-C are a series of charts illustrating data outputs of a DTA system during transitions between reaction stages.
Figure 6B:
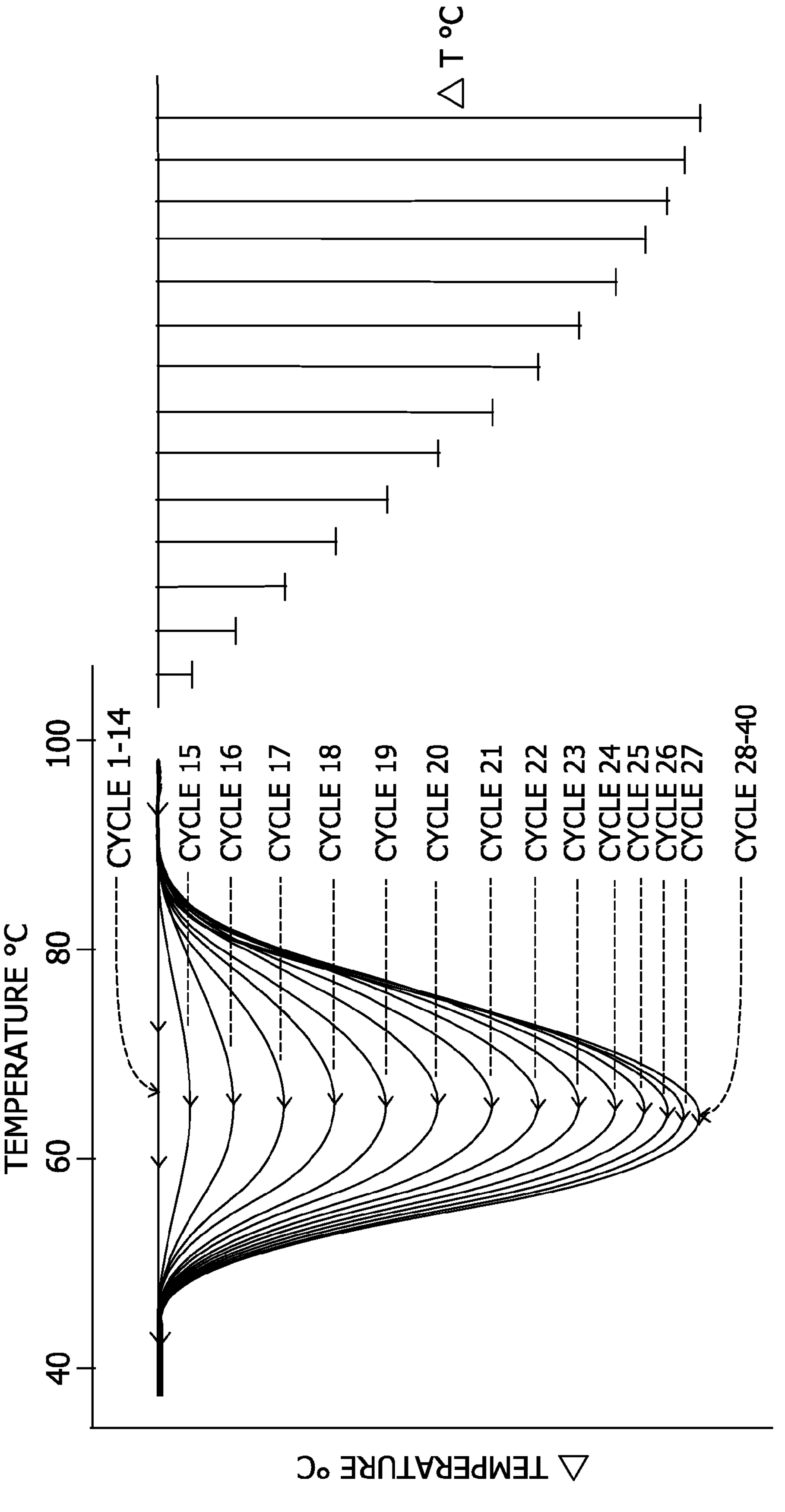
Figure 6C:
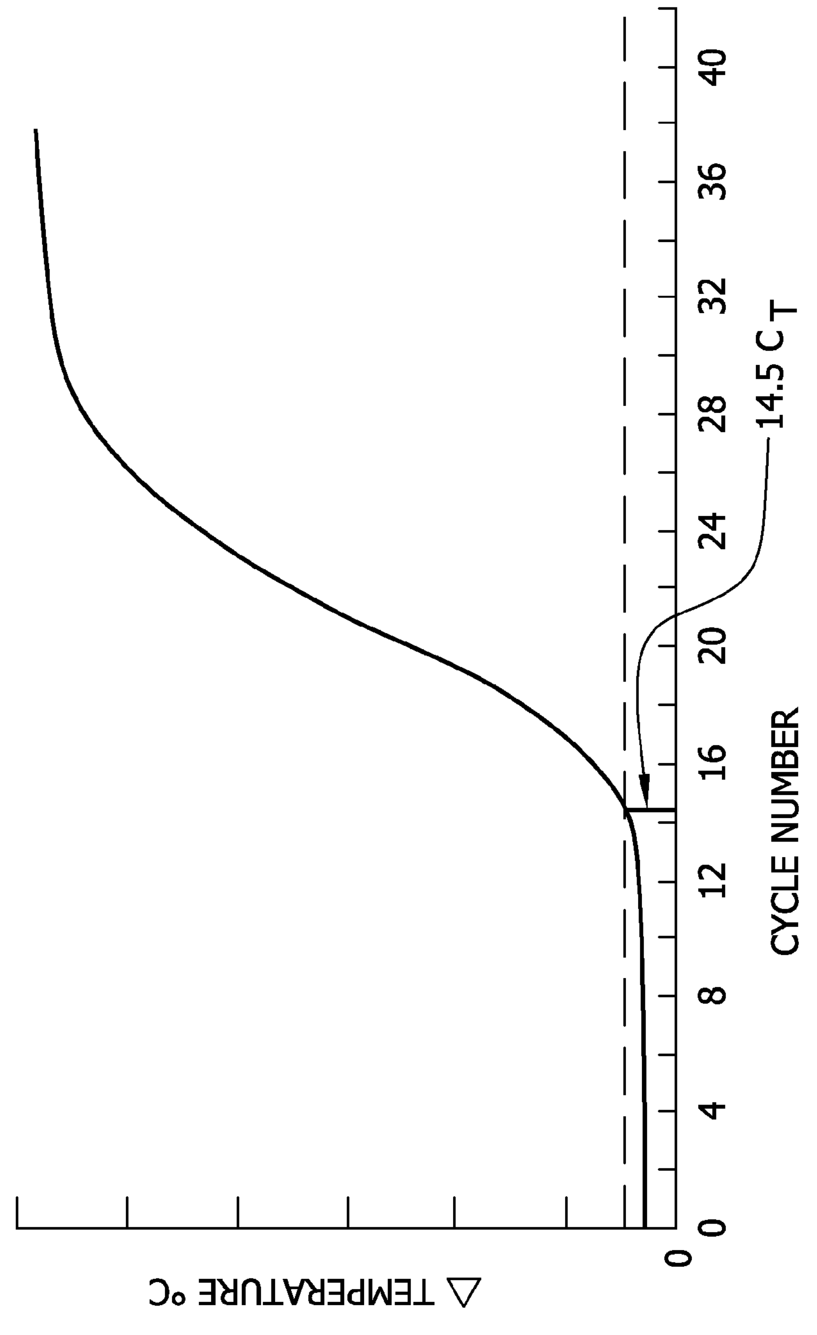

During transitions between the PCR reaction stages, the sample temperature sensors monitor the temperatures of the samples relative to the reference. The difference in temperature during melting and annealing are shown in FIGS. 6A and 6B, respectively, and the resulting thermogram is shown in FIG. 6C. The extra energy required to melt apart the amplified DNA during a rising temperature produces a temperature lag (a differential heat flow) in the samples relative to the reference sample. The energy released from the annealing amplified DNA during a lowering temperature produces temperature excesses (another type of differential heat flow) in the samples relative to the reference sample. These differential heat flows produce differential temperatures measured by the sample temperature sensors indicating presence of amplified DNA.

DSC System

Figure 7:
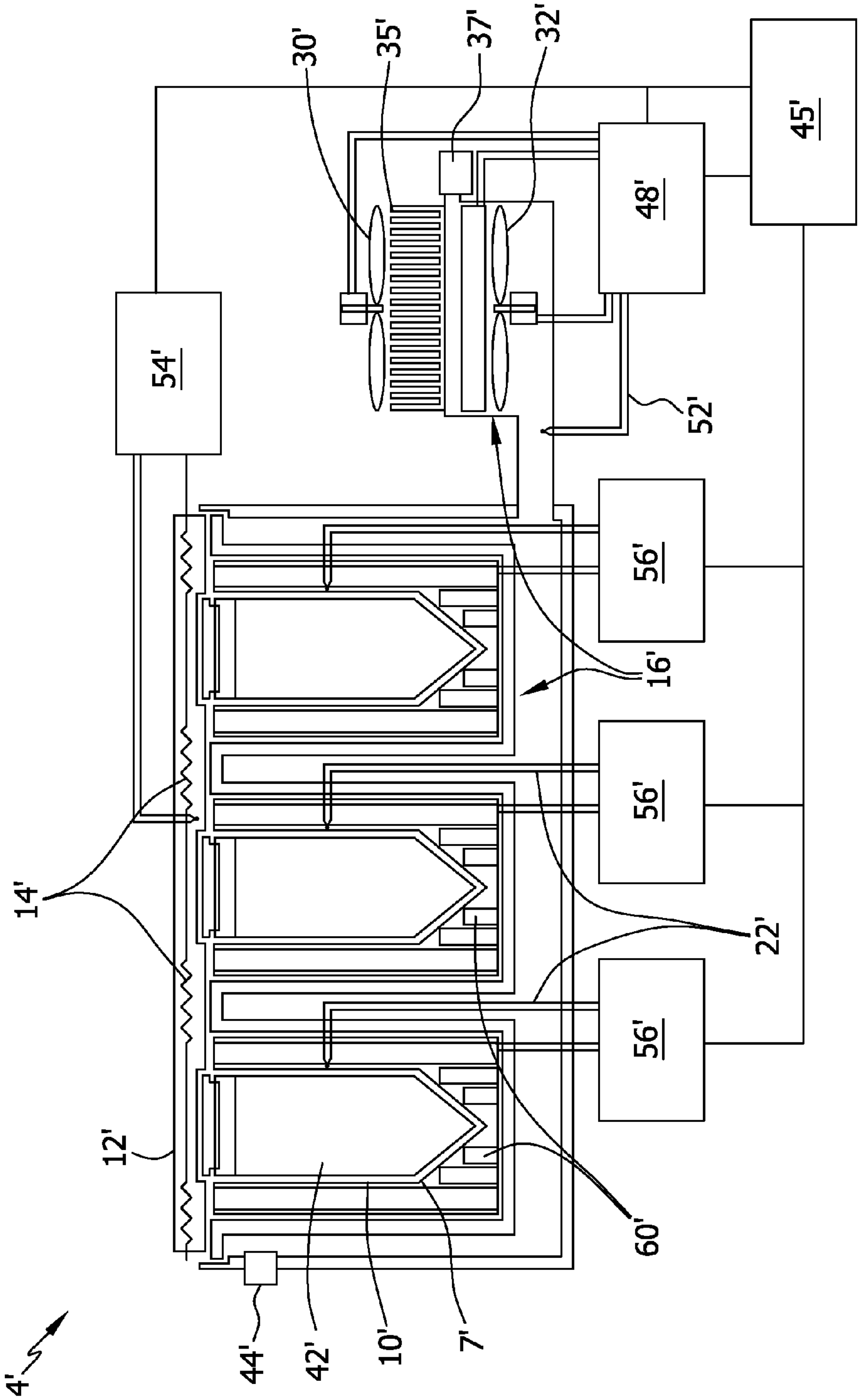
FIG. 7 is a partially schematic cross-section view of a sample block of a second embodiment of the present disclosure with thermal control features being illustrated.
Figure 8:
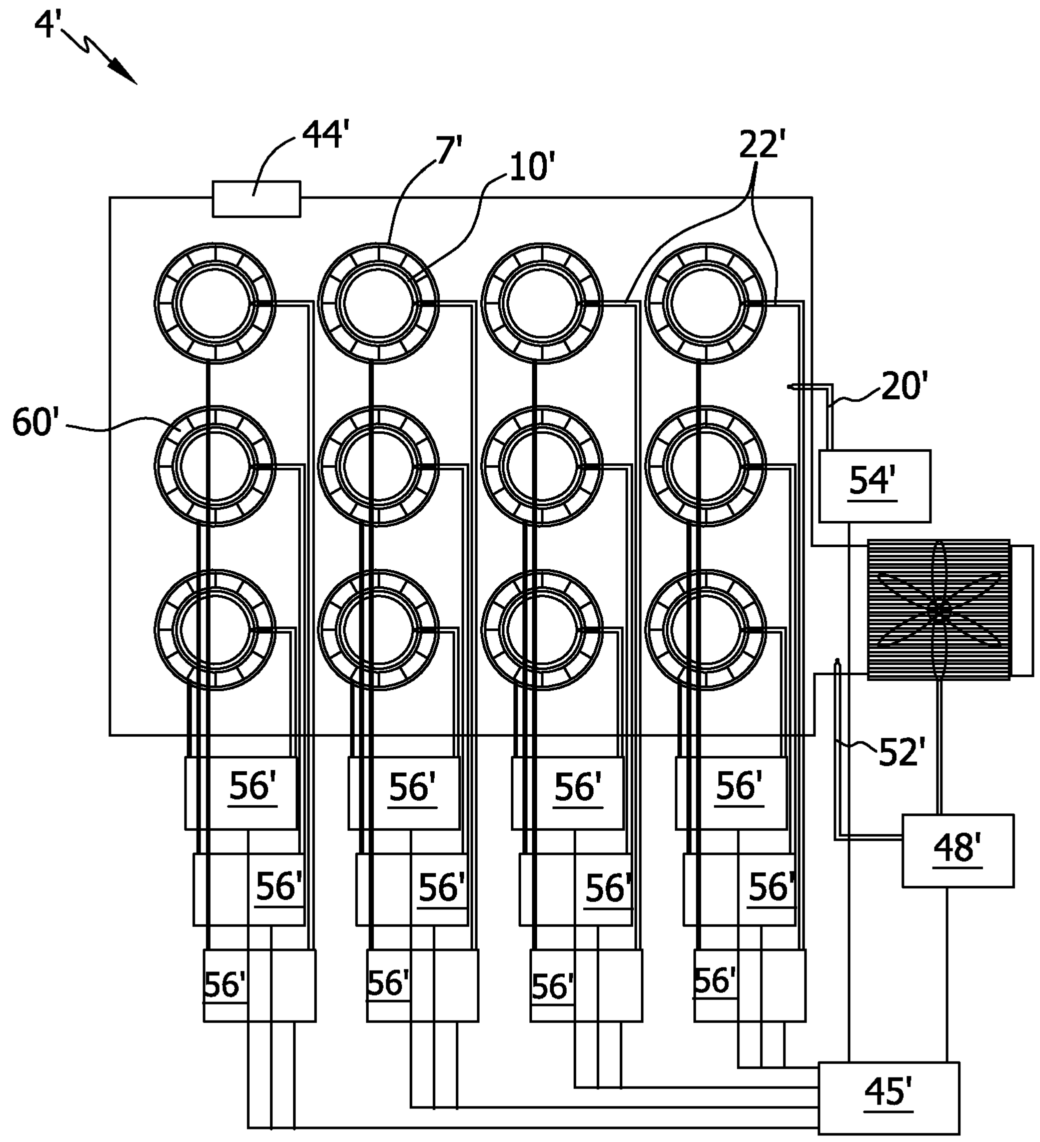
FIG. 8 is a partially schematic top view of the sample block of FIG. 7 with thermal control features being illustrated.

Referring now to FIGS. 7 and 8, a reaction block of a differential scanning calorimetry (DSC) system of one embodiment of the disclosure is generally designated by reference numeral 4'. Generally, the DSC system quantifies the differential heat flow (and temperature) into the samples relative to the reference sample. The DSC system illustrated in FIGS. 7 and 8 is a power compensated system.

While each well of the DTA system illustrated in FIGS. 1 and 2 are in thermal contact with a block heating and cooling system, each well of the DSC system of FIGS. 7 and 8 are at least partially adiabatically isolated as consistent with power compensated systems. Non-power compensated DSC systems may be utilized without departing from the scope of the present disclosure.

The sample block 4' includes a plurality of sample wells 7' therein (12 wells are shown, but any number may be used). Each well 7' is sized and shaped to receive a sample tube 10' therein, and each sample tube is sized to contain the reaction components or samples 42' described above.

A block heating and cooling system 16' supplies heating and cooling to the wells. A Peltier heater/cooler unit is illustrated and other heater/coolers as described above may also be utilized.

The illustrated block heating and cooling system 16' includes an external fan 30', internal fan 32' and heat exchanger 35'. The block heating and cooling system 16 is controlled by a controller unit 48'. The heated/cooled air is circulated into a heating/cooling chamber 40' where the sample wells 7' are located. The air exits the system through an outlet valve 44'. The block heating and cooling system 16' operates similarly to the heating and cooling system 16 described above.

Smaller sample heating and cooling systems 60' are in thermal contact with the samples 42' to apply a smaller adjustment of heating or cooling to the samples an to the reference. Such units may be Peltier heating/cooling units or as otherwise described above. The system 60' may include a block of conducting metals with embedded heaters, or convection heaters that use ducted hot air or cold air.

A sample temperature sensor 22' (e.g., a thermocouple or thermistor) is disposed near the well 7' in contact with the well or actually in the well. Each individual sample temperature is controlled by an individual sample temperature controller 56'. A block temperature sensor 20' (e.g., another thermocouple or thermistor) is disposed distally from the sample and the well 7'. An air temperature sensor 52' monitors the temperature of the air used to heat and cool the samples 42'.

The system further includes a lid 12' for covering the block 4' and the wells 7' therein. The lid 12' includes recesses therein, and each recess is sized to receive a top portion of one of the sample tubes 10'. The lid 12' includes a lid heater 14' for heating the lid, and a lid temperature sensor 18' (e.g., a thermocouple or thermistor). The temperature of the lid 12' may be controlled by a lid temperature controller 54'. A computer 45' or microcontroller is included in the system as described above and by the flow chart of FIG. 3.

While each individual sample temperature is controlled by an individual sample temperature controller 56' in the DSC system illustrated in FIGS. 7 and 8, it is possible to use a single controller that is multiplexed to multiple samples. In such embodiments, the controller analyzes an individual sample or well for a discrete amount of time and then sequences to a second well or sample.

Figure 9:
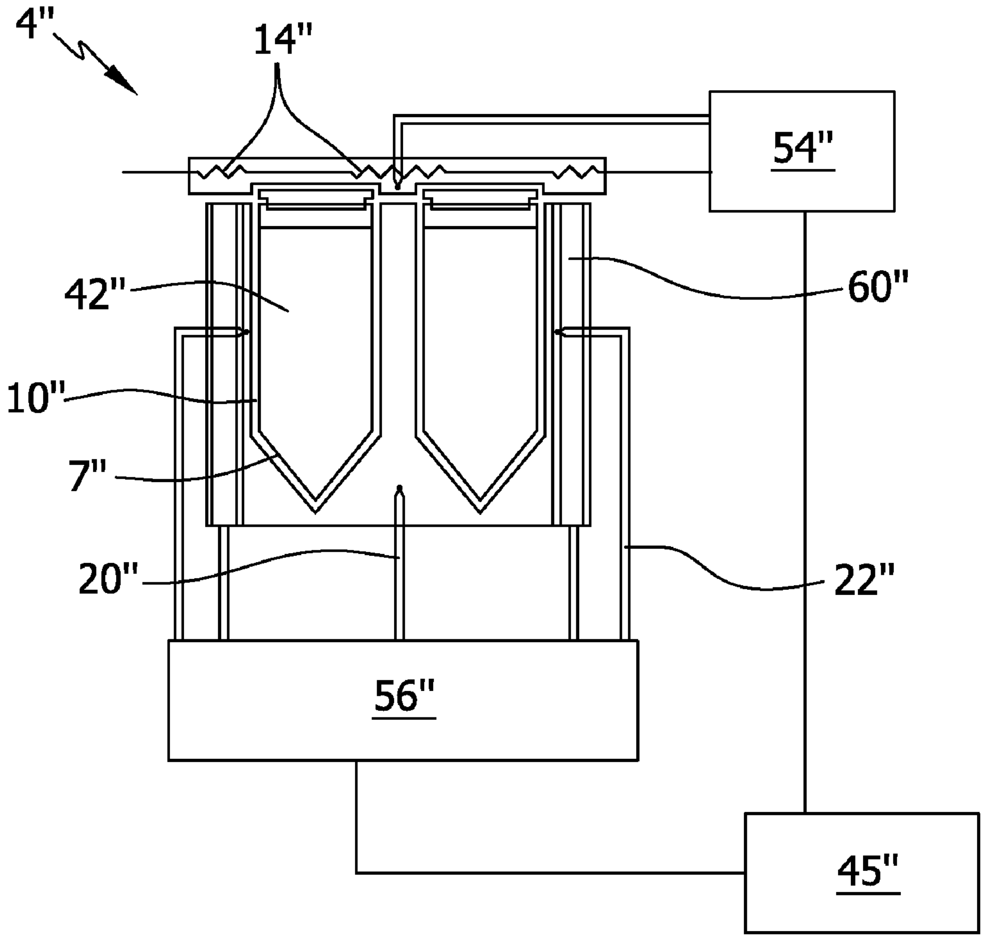
FIG. 9 is a partially schematic cross-section view of a sample block of a third embodiment of the present disclosure with thermal control features being illustrated.
Figure 10:
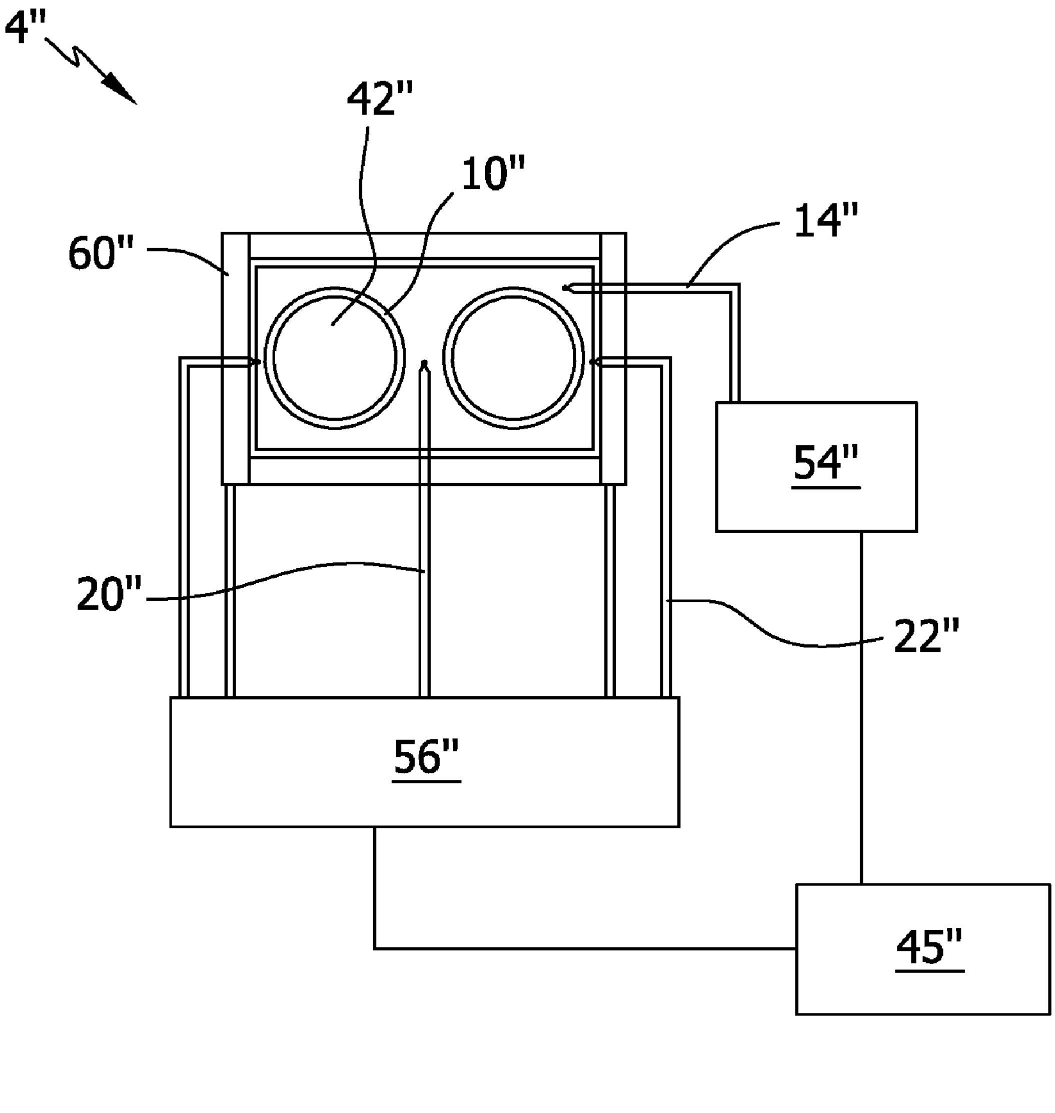
FIG. 10 is a partially schematic top view of the sample block of FIG. 9 with thermal control features being illustrated.

Referring now to FIGS. 9 and 10, a heat flux DSC system of another embodiment of the present disclosure is illustrated. In accordance with heat flux systems, the reaction block 4" includes a paired sample and thermal reference in respective wells 7". While one pair is shown, any number may be used without departing from the scope of the present disclosure. The paired sample and reference are in direct thermal contact with each other. The paired sample and reference are disposed within a single heating and cooling system 60". Enthalpy or heat capacity changes in the sample during amplification of DNA cause a difference in the sample temperature relative to the thermal reference sample. The temperature difference may be measured and related to an enthalpy change by use of known calibration factors.

The temperature of each paired PCR reaction solution and thermal reference solution is controlled by an individual sample temperature controller 56". Sample and reference temperature sensors 22" may be disposed near the well 7" and may be in contact with the well or actually in the well.

Other features of the reaction block 4" are generally similar to the corresponding features of the reaction block 4' of FIGS. 7 and 8 unless otherwise stated. In embodiments with multiple pairs of samples and references, each pair may be controlled by its own temperature controller. Alternatively, a single controller may analyze the multiple pairs. In such embodiments, the controller analyzes an individual pair for a discrete amount of time and then sequences to a second pair.

Generally, the DSC system measures the differential heat flow (and temperature) into the samples relative to a reference. The DSC HF-PCR™ system may be better implemented in a power compensated DSC format, as compared to a heat flux DSC format. In heat flux DSC, direct thermal contact between the sample and reference is required to provide a pathway for the direct flow of heat. Hence, a reference/sample pair is in direct physical contact with each other. In power compensated DSC, individual heater furnaces compensate for the heat flow into the samples relative to a single reference, so that direct physical contact is not required. Power compensated DSC outputs the electrical power consumed by the sample heaters as they compensate for the differential heat flow required to maintain isothermal temperatures of the samples relative to the reference.

The sample power/heat flow profiles match that of the reference until there is a sufficient quantity of newly generated product oligonucleotide. The system cycles until it reaches a cycle threshold ($C_t$) with the computer tracking the number of cycles to reach the $C_t$. The cycle threshold is achieved when the power/heat flow profile of a sample is first detectably different than the reference sample profile.

Figure 11A:
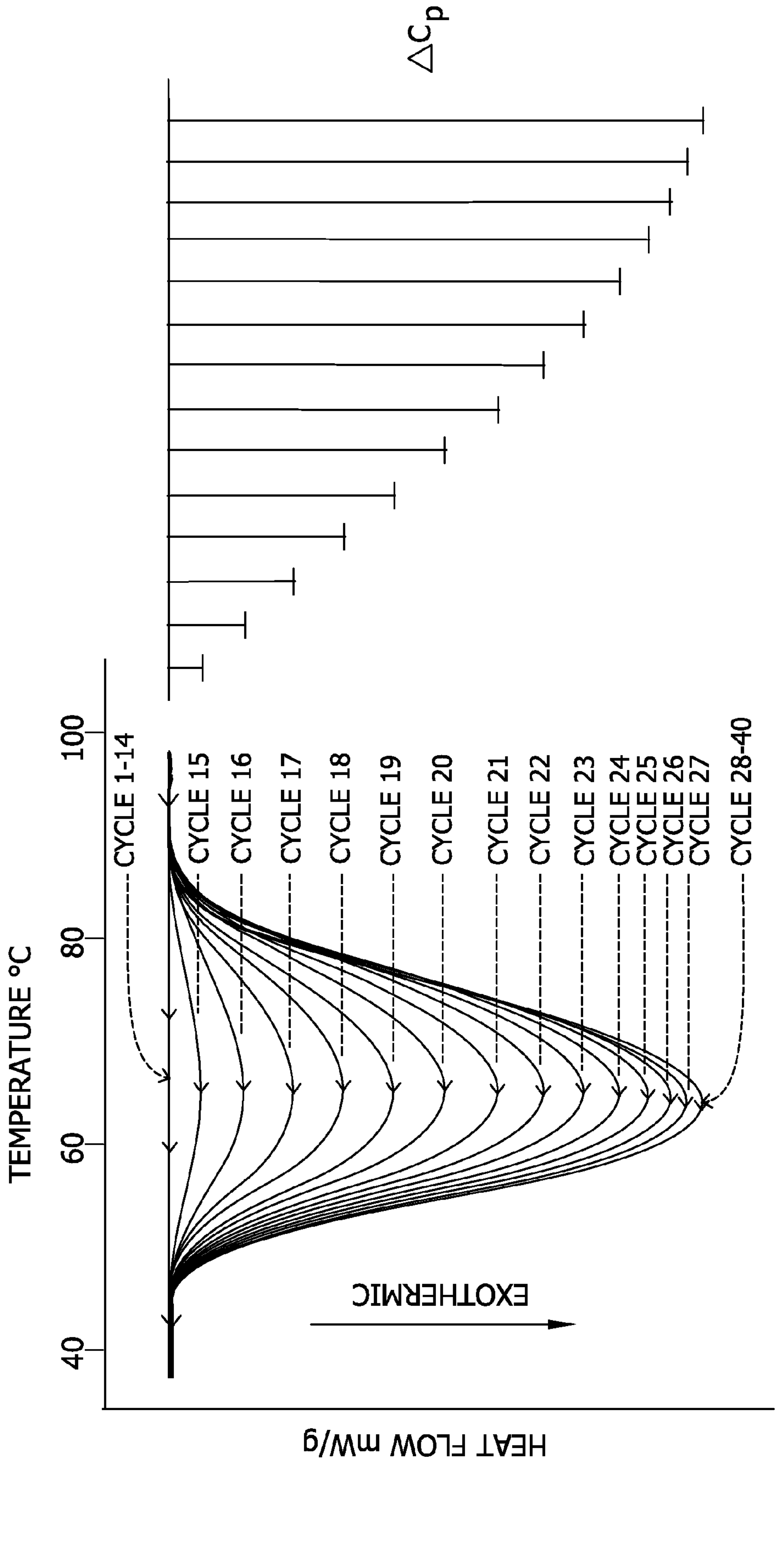
FIGS. 11A-C are a series of charts illustrating data outputs of a DSC system during transitions between reaction stages.
Figure 11B:
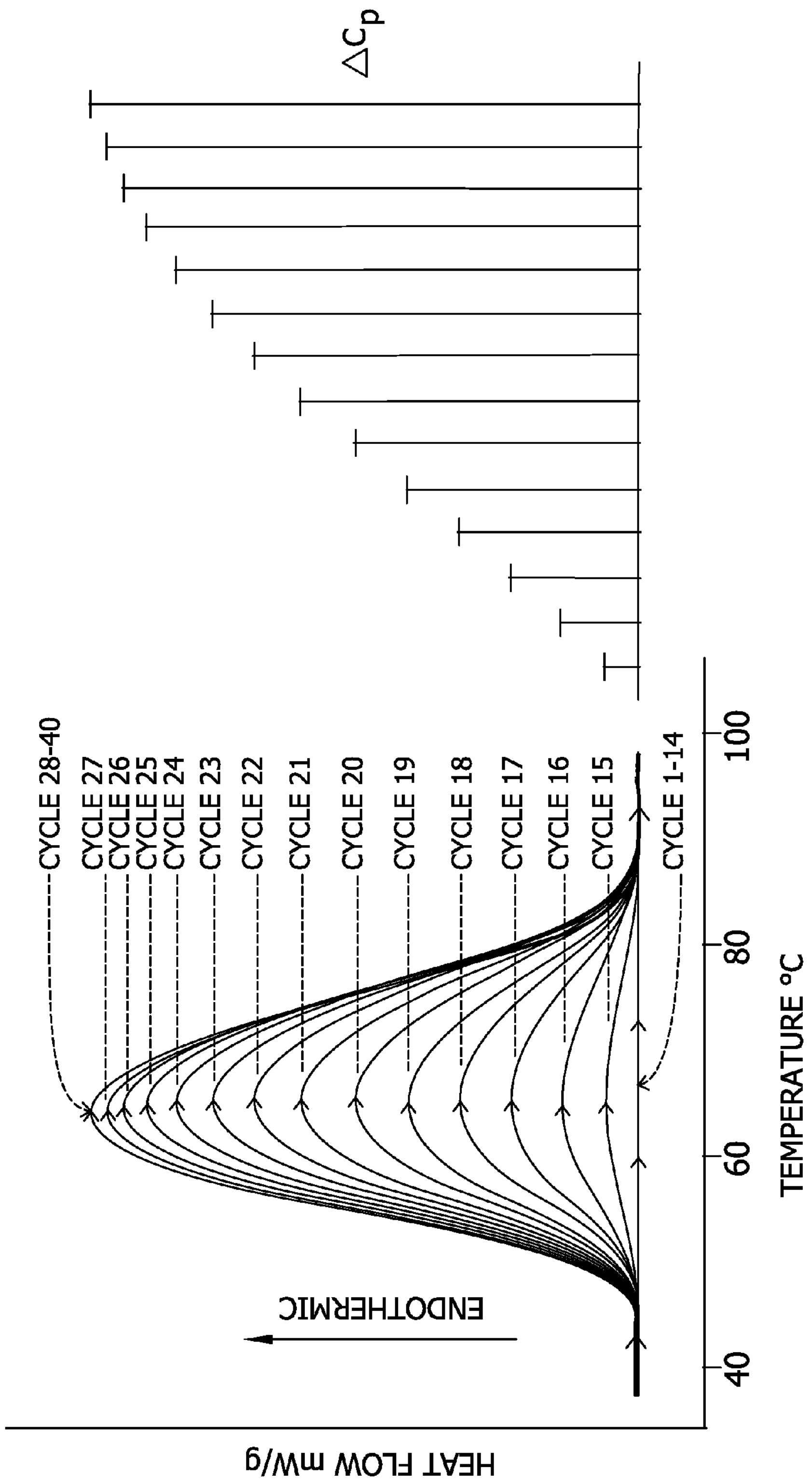
Figure 11C:
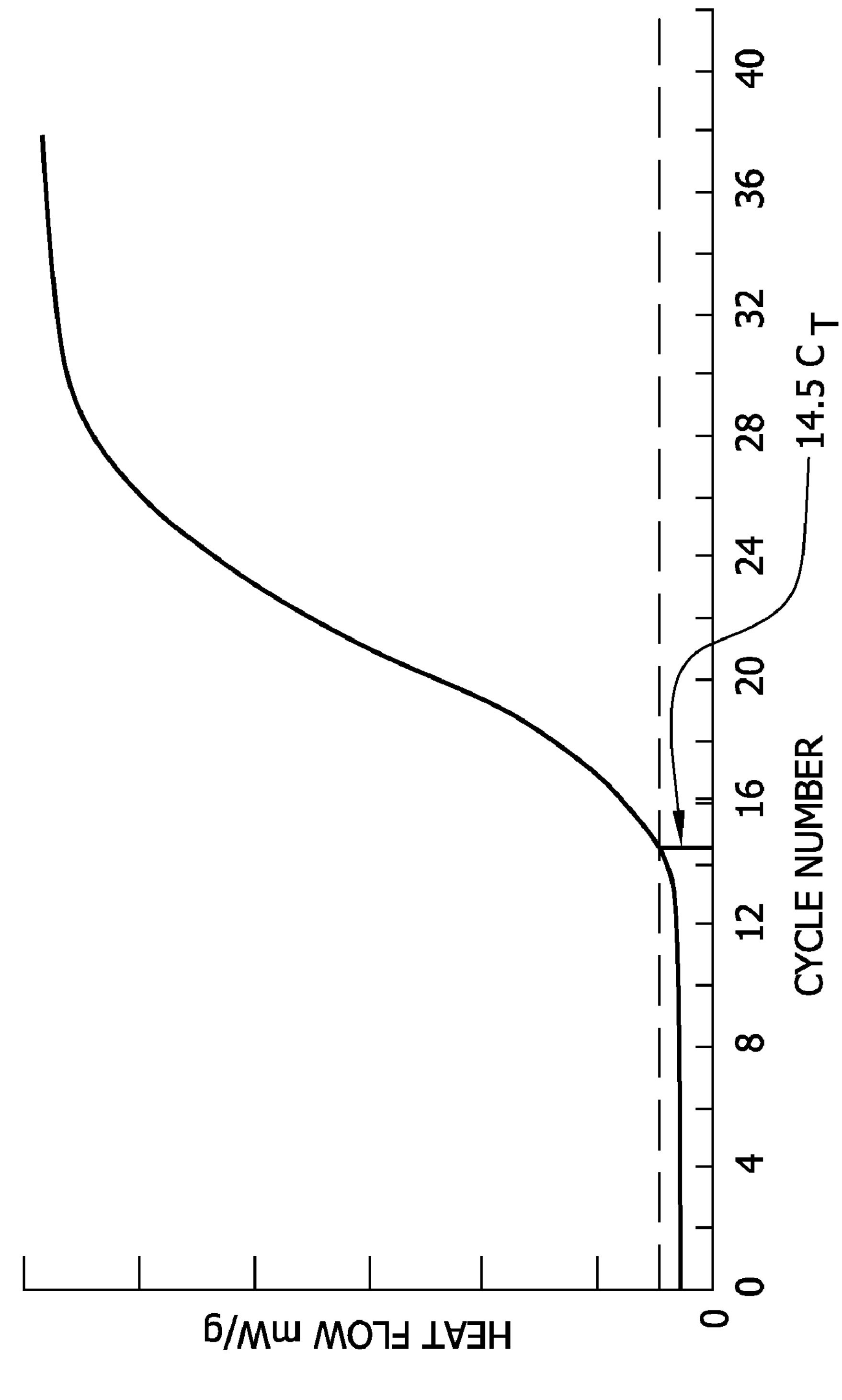

The DSC system allows multiple samples to be analyzed relative to the reference sample (or "samples" as in the case of heat flux DSC). The DSC systems of embodiments of this disclosure are adapted to cycle through 25-40 cycles, while conventional DSC systems cycle through only one or a few temperature ramps or cycles. During the PCR stages, the DSC system transfers heat into the samples for each of the three PCR reaction stages (melting, annealing and elongation). During transitions between the PCR reaction stages, the DSC system monitors the temperatures and power input into the samples relative to the reference. The extra power/heat flow required to melt apart the product amplified DNA during a rising temperature produces a measurable differential heat capacity ΔCp in the samples relative to the reference. The extra energy released from the annealing amplified DNA during a declining temperature also produces a measurable differential heat capacity ΔCp in the samples relative to the reference sample as illustrated in FIG. 11.

The differences between a DTA and power compensated DSC devices include the output data, the control of the DSC furnace compared to the DTA thermal plate and the thermal connection between the wells. The DTA device output data is the differential temperature of the sample well temperature sensor relative to the reference well temperature sensor. In a power compensated DSC device the data output is the differential energy (power) put into the sample heating and cooling system relative to the reference heating and cooling system. The control of this power compensating system is dependent on the sample and temperature sensors and the electronic control circuits. This additional circuitry adds expense and complexity to the DSC devices relative to the DTA devices, which only need a single heating and cooling system control circuit. This is less important in a heat flow DSC system (as compared to power compensated DSC), in which a reference and sample pair are heated in a single furnace and remain in direct thermal contact. The additional control circuitry for power compensated DSC systems relative to DTA systems remains using both convection air heating and the older thermal block heating. Lastly, the DTA systems maintain complete thermal conductivity between the sample wells, while the power compensated DSC systems do not depend on such a connection. In practice, DSC systems may employ a third surrounding heating and cooling system that uniformly heats/cools all sample wells and the independent sample heating and cooling systems only provide the differential power/energy to the individual sample wells.

The systems disclosed herein can be implemented in wide variety of well formats, e.g., a single-well, 8-well, 12-well, 24-well, 96-well, or 384-well format. The systems can also be implemented as a stand-alone microprocessor based system or an integrated system with a personal computer for reaction design, control, and analysis.

When introducing elements of various aspects of the present disclosure or embodiments thereof, the articles "a", "an", "the" and "said" are intended to mean that there are one or more of the elements. The terms "comprising", "including" and "having" are intended to be inclusive and mean that there may be additional elements other than the listed elements. Moreover, the use of "top" and "bottom", "front" and "rear", "above" and "below" and variations of these and other terms of orientation is made for convenience, but does not require any particular orientation of the components.

Various refinements exist of the features noted in relation to the above-mentioned aspects. Further features may also be incorporated in the above-mentioned aspects as well. These refinements and additional features may exist individually or in any combination. For instance, various features discussed herein in relation to any of the illustrated embodiments may be incorporated into any of the above-described aspects, alone or in any combination.

It also will be understood that the systems and methods of the present disclosure can be implemented using any suitable combination of hardware and software. The software (i.e., instructions) for implementing and operating the aforementioned systems and methods can be provided on computer-readable media, which can include without limitation, firmware, memory, storage devices, micro controllers, microprocessors, integrated circuits, ASICS, on-line downloadable media, and other available media.

As various changes could be made in the above constructions, methods and products without departing from the scope of the disclosure, it is intended that all matter contained in the above description or shown in the accompanying drawings shall be interpreted as illustrative and not in a limiting sense. Further, all dimensional information set forth herein is exemplary and is not intended to limit the scope of the disclosure.

What is claimed is:

1. A method, comprising:
- applying heat to a PCR reaction solution;
- applying heat to a thermal reference solution;
- measuring a temperature of the PCR reaction solution and a temperature of the thermal reference solution during each of a plurality of cycles;
- comparing the temperature of the PCR reaction solution to the temperature of the thermal reference solution during each cycle from the plurality of cycles; and
- detecting the formation of amplified DNA within the PCR reaction solution when a difference between a temperature of the PCR reaction solution and a temperature of the thermal reference solution is greater than a threshold temperature difference.

2. A method as set forth in claim 1, wherein the temperature of the PCR reaction solution and the temperature of the thermal reference solution are measured as heat is applied.

3. A method as set forth in claim 1, further comprising:
- charging a sample well with a reaction buffer, a template DNA, a DNA polymerase and one or more deoxynucleotide triphosphates to form the PCR reaction solution; and
- amplifying the template DNA to produce the amplified DNA in the PCR reaction solution.

4. A method as set forth in claim 3 wherein the PCR reaction solution is degassed prior to amplification.

5. A method as set forth in claim 3, wherein the sample well is a first sample well, the template DNA is a first template DNA, the method further comprising:
- charging a second sample well with reaction buffer, a second template DNA, DNA polymerase and deoxynucleotide triphosphates to form a second PCR reaction solution;
- amplifying the second template DNA to produce a second amplified DNA in the second PCR reaction solution;
- applying heat to the second PCR reaction solution;
- measuring the temperature of the second PCR reaction solution;
- comparing the temperature of the second PCR reaction solution and the temperature of the thermal reference solution to detect formation of the second amplified DNA.

6. A method as set forth in claim 5, wherein the first template DNA and the second template DNA are amplified simultaneously and formation of the first amplified DNA and the second amplified DNA are detected simultaneously.

7. A method as set forth in claim 3, wherein the thermal reference solution includes an amount of reaction buffer, the reaction buffer having substantially the same composition as the reaction buffer utilized to form the PCR reaction solution.

8. A method as set forth in claim 3, wherein the thermal reference solution includes an amount of reaction buffer and deoxynucleotide triphosphates, the reaction buffer and deoxynucleotide triphosphates having substantially the same respective compositions as the reaction buffer and deoxynucleotide triphosphates utilized to form the PCR reaction solution.

9. A method as set forth in claim 3, wherein primer oligonucleotides are charged to the sample well to form the PCR reaction solution and the thermal reference solution includes an amount of reaction buffer, deoxynucleotide triphosphates and primer oligonucleotides, the reaction buffer, deoxynucleotide triphosphates and primer oligonucleotides having substantially the same respective compositions as the reaction buffer, deoxynucleotide triphosphates and oligonucleotides utilized to form the PCR reaction solution.

10. A method as set forth in claim 1, wherein heat is applied to the PCR reaction solution and heat is applied to the thermal reference solution during each of the plurality of cycles.

11. A method as set forth in claim 1, wherein the detecting is performed without the use of optics, gel electrophoresis, oligonucleotide sequencing or fluorescence.

12. A method as set forth in claim 1, wherein a mass of the PCR reaction solution is substantially equal to a mass of the thermal reference solution.

13. A method as set forth in claim 1, wherein the PCR reaction solution includes an additive that increases the heat of melting of DNA.

14. A method of detecting the formation of amplified DNA in a PCR reaction solution during or after PCR amplification, the method, comprising:
- generating heat from a first heater and applying the heat to the PCR reaction solution;
- generating heat from a second heater and applying the heat to a thermal reference solution;
- measuring a power input to the first heater and measuring a power input to the second heater; and
- detecting the formation of amplified DNA within the PCR reaction solution based on a difference in the power input to the first heater and the power input to the second heater.

15. A method as set forth in claim 14, further comprising:
- comparing the power input to the first heater and the power input to the second heater to detect formation of the amplified DNA.

16. A method as set forth in claim 14 wherein the power input to the first heater and the power input to the second heater are measured as heat is applied.

17. A method as set forth in claim 14, further comprising:
- charging a sample well with a reaction buffer, a template DNA, a DNA polymerase and deoxynucleotide triphosphates to form the PCR reaction solution; and
- amplifying the template DNA to produce the amplified DNA in the PCR reaction solution.

18. A method as set forth in claim 17 wherein the PCR reaction solution is degassed prior to amplification.

19. A method as set forth in claim 17, wherein the PCR reaction solution is a first PCR reaction solution, the template DNA is a first template DNA, the amplified DNA is a first amplified DNA, the method further comprising:
- charging a second sample well with reaction buffer, a second template DNA, DNA polymerase and deoxynucleotide triphosphates to form a second PCR reaction solution;
- amplifying the second template DNA to produce a second amplified DNA in the second PCR reaction solution;
- generating heat from a third heater and applying the heat to the second amplified DNA;
- measuring the power input to the third heater; and
- comparing the power input to the third heater and the power input to the second heater to detect formation of a second amplified DNA.

20. A method as set forth in claim 19, wherein the first template DNA and the second template DNA are amplified simultaneously and wherein formation of the first amplified DNA and the second amplified DNA are detected simultaneously.

21. A method as set forth in claim 17, wherein the thermal reference solution includes an amount of reaction buffer, the reaction buffer having substantially the same composition as the reaction buffer utilized to form the PCR reaction solution.

22. A method as set forth in claim 17, wherein the thermal reference solution includes an amount of reaction buffer and deoxynucleotide triphosphates, the reaction buffer and deoxynucleotide triphosphates having substantially the same respective compositions as the reaction buffer and deoxynucleotide triphosphates utilized to form the PCR reaction solution.

23. A method as set forth in claim 17, wherein primer oligonucleotides are charged to the sample well to form the PCR reaction solution and the thermal reference solution includes an amount of reaction buffer, deoxynucleotide triphosphates and primer oligonucleotides, the reaction buffer, deoxynucleotide triphosphates and primer oligonucleotides having substantially the same respective compositions as the reaction buffer, deoxynucleotide triphosphates and oligonucleotides utilized to form the PCR reaction solution.

24. A method as set forth in claim 14 wherein heat is applied to the PCR reaction solution and the thermal reference solution during a plurality of cycles and a temperature of the PCR reaction solution and a temperature of the thermal reference solution are each measured after the plurality of cycles are complete.

25. A method as set forth in claim 14, wherein heat is applied to the PCR reaction solution and heat is applied to the thermal reference solution during a plurality of cycles and a temperature of the PCR reaction solution and a temperature of the thermal reference solution are each measured during the plurality of cycles.

26. A method as set forth in claim 14, wherein the detecting is performed without the use of optics, gel electrophoresis, oligonucleotide sequencing or fluorescence.

27. A method as set forth in claim 14, wherein a mass of the PCR reaction solution is substantially equal to a mass of the thermal reference solution.

28. A method as set forth in claim 14, wherein the PCR reaction solution includes an additive that increases the heat of melting of DNA.

29. A method, comprising:

applying heat to a PCR reaction solution during each of a plurality of cycles;

applying heat to a thermal reference solution during each of the plurality of cycles;

measuring a temperature of the PCR reaction solution and a temperature of the thermal reference solution during each cycle from the plurality of cycles;

comparing the temperature of the PCR reaction solution to the temperature of the thermal reference solution during at least one cycle from the plurality of cycles to determine a difference between the temperatures; and relating the difference in temperature between the PCR reaction solution and the thermal reference solution to an enthalpy change in the PCR reaction solution to detect a formation of amplified DNA within the PCR reaction solution.

30. A method as set forth in claim 29, wherein the temperature of the PCR reaction solution and the temperature of the thermal reference solution are each measured as heat is applied to the PCR reaction solution and as heat is applied to the thermal reference solution.

31. A method as set forth in claim 29 further comprising:

charging a sample well with a reaction buffer, a template DNA, a DNA polymerase and one or more deoxynucleotide triphosphates to form the PCR reaction solution; and amplifying the template DNA to produce the amplified DNA in the PCR reaction solution.

32. A method as set forth in claim 31 wherein the PCR reaction solution is degassed prior to amplification.

33. A method as set forth in claim 31, wherein the sample well is a first sample well, the template DNA is a first template DNA, the method further comprising:

charging a second sample well with a reaction buffer, a second template DNA, a DNA polymerase and one or more deoxynucleotide triphosphates to form a second PCR reaction solution;

amplifying the second template DNA to produce a second amplified DNA in the second PCR reaction solution;

applying heat to the second PCR reaction solution;

measuring a differential temperature between the second PCR reaction solution and the thermal reference solution.

34. A method as set forth in claim 33, wherein the first template DNA and the second template DNA are amplified simultaneously and the formation of the first amplified DNA and the formation of the second amplified DNA are detected simultaneously.

35. A method as set forth in claim 31 wherein the thermal reference solution includes an amount of reaction buffer, the reaction buffer having substantially the same composition as the reaction buffer utilized to form the PCR reaction solution.

36. A method as set forth in claim 31 wherein the thermal reference solution includes an amount of reaction buffer and deoxynucleotide triphosphates, the reaction buffer and deoxynucleotide triphosphates having substantially the same respective compositions as the reaction buffer and deoxynucleotide triphosphates utilized to form the PCR reaction solution.

37. A method as set forth in claim 31 wherein primer oligonucleotides are charged to the sample well to form the PCR reaction solution and the thermal reference solution includes an amount of reaction buffer, deoxynucleotide triphosphates and primer oligonucleotides, the reaction buffer, deoxynucleotide triphosphates and primer oligonucleotides having substantially the same respective compositions as the reaction buffer, deoxynucleotide triphosphates and oligonucleotides utilized to form the PCR reaction solution.

38. A method as set forth in claim 29 wherein a temperature of the PCR reaction solution and a temperature of the thermal reference solution are measured after the plurality of cycles are complete.

39. A method as set forth in claim 29, wherein the detection of the formation of amplified DNA within the PCR reaction solution is performed without the use of optics, gel electrophoresis, oligonucleotide sequencing or fluorescence.

40. A method as set forth in claim 29, wherein a mass of the PCR reaction solution is substantially equal to a mass of the thermal reference solution.

41. A method as set forth in claim 29, wherein the PCR reaction solution includes an additive that increases the heat of melting of DNA.

42. A method, comprising:

applying heat to a PCR reaction solution during each of a plurality of cycles;

applying heat to a thermal reference solution during each of the plurality of cycles;

measuring a temperature of the PCR reaction solution and a temperature of the thermal reference solution during at least one of the plurality of cycles; and detecting a formation of amplified DNA within the PCR reaction solution based on the measured temperatures and without the use of optics, gel electrophoresis, or fluorescence detection techniques.

* * * * *